United States Patent
Eliasson et al.

(10) Patent No.: US 9,493,408 B2
(45) Date of Patent: Nov. 15, 2016

(54) REMOVAL OF AMMONIA IN UREA FINISHING

(75) Inventors: Johanna Eliasson, Lund (SE); Ylva Eriksson, Lund (SE); David Holmström, Lund (SE); P. Christian Hulteberg, Malmö (SE); Hans T. Karlsson, Lund (SE); Filip Nilsson, Lund (SE); Frida Ojala, Lund (SE); Johan Albert Arno Van Den Tillaart, Mèlick (NL)

(73) Assignee: STAMICARBON B.V., Sittard (NL)

( * ) Notice: Subject to any disclaimer, the term of this patent is extended or adjusted under 35 U.S.C. 154(b) by 273 days.

(21) Appl. No.: 13/578,293

(22) PCT Filed: Feb. 12, 2010

(86) PCT No.: PCT/NL2010/050069
§ 371 (c)(1),
(2), (4) Date: Sep. 6, 2012

(87) PCT Pub. No.: WO2011/099844
PCT Pub. Date: Aug. 18, 2011

(65) Prior Publication Data
US 2012/0330060 A1  Dec. 27, 2012

(51) Int. Cl.
*C07C 273/04* (2006.01)
*B01D 53/58* (2006.01)

(52) U.S. Cl.
CPC ............. *C07C 273/04* (2013.01); *B01D 53/58* (2013.01); *B01D 2253/102* (2013.01); *B01D 2253/108* (2013.01); *Y02P 20/142* (2015.11); *Y02P 20/582* (2015.11)

(58) Field of Classification Search
CPC ................ C07C 273/04; B01D 53/58; B01D 2253/102; B01D 2253/108; Y02P 20/142; Y02P 20/582
USPC ............................................. 564/67; 95/128
See application file for complete search history.

(56) References Cited

U.S. PATENT DOCUMENTS

| | | | |
|---|---|---|---|
| 3,191,916 A | | 6/1965 | Kurpit et al. |
| 3,485,014 A | * | 12/1969 | Nishimoto et al. ............. 95/110 |
| 4,832,839 A | * | 5/1989 | Tamura ......................... 210/188 |
| 6,261,345 B1 | | 7/2001 | Miyano et al. |
| 6,818,043 B1 | * | 11/2004 | Chang et al. ..................... 95/37 |
| 7,622,609 B2 | | 11/2009 | Mennen et al. |
| 7,817,891 B2 | | 10/2010 | Lavenne et al. |
| 2006/0039847 A1 | * | 2/2006 | Kaboord et al. ............. 423/359 |
| 2007/0287863 A1 | * | 12/2007 | Romiti ............................ 564/66 |

FOREIGN PATENT DOCUMENTS

| | | | |
|---|---|---|---|
| CA | 2036746 | * | 2/1992 |
| CA | 2723850 A1 | | 11/2009 |
| CN | 1266733 A | | 9/2000 |
| CN | 101501398 A | | 8/2009 |
| EP | 1980887 A1 | | 10/2008 |
| JP | 62042736 | | 2/1987 |
| WO | 0246145 A1 | | 6/2002 |
| WO | WO2009/138178 | * | 11/2009 ............. B01D 53/58 |

OTHER PUBLICATIONS

Helminen et al., "Comparision of Sorbents and Isotherm Models for NH3-Gas Separation by Adsorption," AIChE Journal, 46(8), 1541-1555, 2000.*
Reddy et al., "Sorption Properties of Cation-Exchanged B-Zeolites," J. Phys. Chem., 96, 7923-7928, 1992.*
International Search Report, dated Nov. 4, 2010, issued in priority International Application No. PCT/NL2010/050069.

* cited by examiner

*Primary Examiner* — Paul A Zucker
*Assistant Examiner* — Mark Luderer
(74) *Attorney, Agent, or Firm* — Gianna J. Arnold; Saul Ewing LLP

(57) ABSTRACT

Disclosed is a method for the removal of ammonia from the off-gas of a finishing section of a urea production plant. The method comprises contacting the off-gas with a solid adsorbent capable of physically adsorbing ammonia, particularly activated carbon or zeolite. Thereupon the solid adsorbent having ammonia adsorbed thereon is separated from the gas and regenerated by dissolving ammonia in an extraction liquid, preferably water. After separating the water from the solid adsorbent, the latter is re-used in the process.

17 Claims, 1 Drawing Sheet

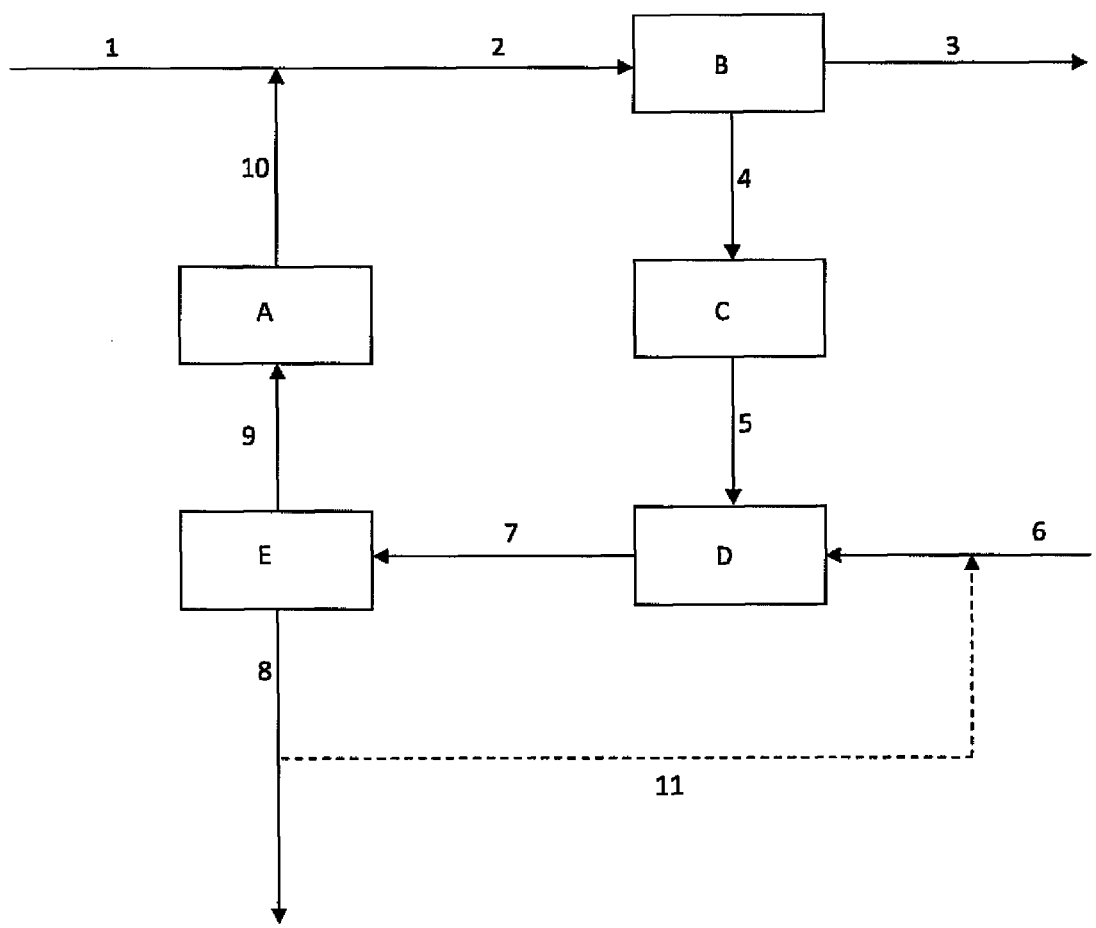

REMOVAL OF AMMONIA IN UREA FINISHING

CROSS REFERENCE TO RELATED APPLICATIONS

This application claims the priority of PCT/NL2010/050069, filed on Feb. 12, 2010, the entire contents of which is hereby incorporated in total by reference.

FIELD OF THE INVENTION

The invention is in the field of the removal of ammonia from the off-gas of a finishing section of a urea production plant. Particularly, the invention pertains to the reduction of the continuous ammonia emission occurring from such a urea plant finishing section.

BACKGROUND OF THE INVENTION

Urea is produced from ammonia and carbon dioxide. Today's urea production involves relatively clean processes, particularly low in the emission of urea dust and ammonia. However, besides the chemical synthesis of urea, the production of urea on a commercial scale requires that the urea be presented in a suitable solid, particulate form. To this end, urea production involves a finishing step in which a urea melt is brought into the desired particulate form, generally involving any one of prilling, granulation, and pelletizing.

Prilling used to be the most common method, in which the urea melt is distributed in a prilling tower and the droplets solidify as they fall down. However, the end-product is often desired to have a larger diameter and higher crushing strength than the one resulting from the prilling technique. These drawbacks led to the development of the fluidized bed granulation technique, where the urea melt is sprayed on granules that grow in size as the process continues. Prior to the injection in the granulator, formaldehyde is added to prevent caking and to give strength to the end-product.

The air that leaves the finishing section contains urea dust and ammonia. The latter is particularly caused by an unwanted side-reaction in the finishing step, viz. the formation of biuret, i.e. a dimerization of urea, with release of ammonia. Another side-reaction that may occur is hydrolysis of urea, again with release of ammonia. Thus, despite the relatively clean nature of the urea synthesis, the commercial production of urea inevitably goes with the formation of ammonia. This ammonia is normally emitted through the off-gas of the finishing section of a urea plant.

With a view to increased demand for urea production, and increased legal and environmental requirements as to reduce the level of emission of ammonia, it is desired that the ammonia specifically emitted in urea finishing, be prevented or removed. This is particularly challenging, since the amounts of off-gas (mainly air) are enormous, and the concentration of ammonia is low. A typical airstream is of the order of 750,000 $Nm^3/h$. A typical concentration of ammonia therein is 100 $mg/Nm^3$.

The relatively low concentration of ammonia means that the off-gas of a finishing section of a urea production plant does not lend itself to ammonia removal by conventional techniques such as wet scrubbing. Rather, the state of the art in the present field is the removal of ammonia by means of acid. Whilst this leads to very efficient removal of ammonia, it presents a serious drawback in that it results in a by-product, viz. the corresponding ammonium salt. This itself needs then to be disposed of, i.e. the emission problem is effectively traded for another problem of chemical waste.

It is therefore desired to provide a method by which the ammonia from the off-gas of a finishing section of a urea production plant can be removed without causing the formation of a new by-product.

Other methods of removing ammonia from gas are known. Background references include the following.

Helminen et al., AIChE Journal August 2000, Vol. 46 No. 8, pages 1541-1555 presents a comparison of adsorbents and isotherm models for ammonia separation by adsorption. Helminen recognizes that ammonia-gas separation by adsorption and recovery for re-use is well-known, but has not been applied extensively. In this respect reference is made to problems related to the selectivity, capacity and regenerability of the adsorbents. It is indicated that most applications of adsorbents are related to the separation of ammonia from the gas streams in the production process of ammonia. Zeolite, alumina, silica gel and active carbon are mentioned as being used for this purpose. Helminen thereupon presents a study into which of these adsorbents would work best. Ammonia was considered to adsorb most strongly on certain zeolites (13X and 4A). The thrust of Helminen's study, however, is to identify the best models for studying adsorption isotherms, and no practical use of the adsorbents is suggested.

In WO 00/40324 a method is disclosed for the separation of ammonia gas and a solid adsorbent composition. It outlines several problems with the removal of ammonia from gas streams, discussing wet scrubbing, including absorption into acid solutions with the formation of salts as mentioned above, as well as gas adsorption over a solid adsorbent bed with regeneration of adsorbent. In the latter case, an indicated problem is that ammonia is adsorbed very strongly onto many conventional adsorbents such as zeolites, alumina, and silica gel, which is said to cause the adsorption isotherms to be unfavorable for desorption, making adsorbent regeneration difficult. This is said to be different for activated carbon, which can be regenerated simply by depressurizing, but the activated carbon comes with a low selectivity and adsorption capacity for ammonia. As a solution, the reference presents the use of a solid copper (I) containing adsorbent.

Bernal et al., Bioresource Technology 43 (1993), 27-33 relates to certain zeolites as adsorbents for ammonia and ammonium. This reference too focuses on the pertinent adsorption isotherms. The desorption of ammonia, and regeneration of the adsorbent, is not addressed.

A further peculiarity of the off-gas of a finishing section of a urea production plant, is that it not only comprises ammonia, but also urea dust. It would be desired if a method could be provided that would not only serve to remove ammonia from the off-gas, but also urea dust.

All in all, it is desired to provide a method of removing ammonia specifically from a finishing section of a urea production plant. It is moreover desired that this goes without the formation of yet another by-product. It is further desired that the method enables the removal of urea dust from the off-gas as well.

SUMMARY OF THE INVENTION

In order to better address one or more of the foregoing desires, the invention, in one aspect, presents a method for the removal of ammonia from the off-gas of a finishing section of a urea production plant, comprising (a) contacting the off-gas with a solid adsorbent capable of physically adsorbing ammonia and
(b) separating the solid adsorbent having ammonia adsorbed thereon from the gas.

The invention, in another aspect, provides the use of a solid adsorbent capable of physically adsorbing ammonia, for the removal of ammonia from the off-gas of a finishing section of a urea production plant.

In yet another aspect, the invention concerns a method for the removal of ammonia and urea dust from the off-gas of a finishing section of a urea production plant, comprising contacting the off-gas with a solid adsorbent capable of physically adsorbing ammonia, subjecting the off-gas to a solid-gas separation step and regenerating the adsorbent by dissolving the ammonia adsorbed thereon in water.

In a still further aspect, the invention is a process for the production of urea comprising reacting ammonia and carbon dioxide under conditions so as to form urea, and subjecting the urea to a melt finishing step so as to form particulate urea and off-gas, wherein ammonia, and preferably also urea dust, is removed from the off-gas by a method comprising the above steps (a) and (b).

DETAILED DESCRIPTION OF THE INVENTION

General Considerations

The invention, in a broad sense, resides in the judicious choice of solid adsorbents, capable of physically adsorbing ammonia, for removing ammonia from the off-gas of a finishing section of a urea production plant.

Although the invention thus broadly, pertains to the adsorption as such, it will be understood that a preferred, economically viable process will not stop at the adsorption step, but will further allow regenerating, and re-using, the adsorbent and possibly also the removed ammonia.

In selecting solid adsorbents for this purpose, the invention particularly makes use of the recognition that an optimal balance of removal of ammonia through adsorption and regenerability of the adsorbent, can be achieved on the basis of physical adsorption (also known as physisorption).

This does not mean that, particularly in the case of high capacity adsorbents such as zeolites, ammonia would not also adsorb more strongly, viz. through chemical adsorption (chemisorption, in fact chemical bonding). However, in one aspect, the invention is based on the recognition that the amount of ammonia adsorbed by physisorption is much larger than the chemisorbed amount. Rather contrary to regular thinking in the art, this has led the inventors to postulate that if the physisorbed ammonia can be desorbed, a sufficient part of the adsorbent is in fact regenerated.

Based on the foregoing recognition, the invention, in another aspect, results in avoiding the unfavorable adsorption isotherms in the step of desorption. In the art, desorption is attempted by depressurizing, and/or by high temperature treatment, and/or by steam (in which case it is particularly the hot vapor that should do the desorption, i.e. again a process driven by conditions of temperature and pressure). In the present invention, the desorption is conducted on the basis of the water-solubility of ammonia. The fact that this may not remove more strongly bound, chemisorbed, ammonia, surprisingly does not hamper the regenerability of the adsorbent. Therewith, in a counter-intuitive way, the present invention bypasses the otherwise challenging choice between adsorption capacity and regenerability.

Thus the invention, in a preferred embodiment, provides a method for the removal of ammonia from the off-gas of a finishing section of a urea production plant, comprising
(a) contacting the off-gas with a solid adsorbent capable of physically adsorbing ammonia;
(b) separating the solid adsorbent having ammonia adsorbed thereon from the gas; and
(c) regenerating the solid adsorbent by dissolving ammonia in an extraction liquid, preferably water, and separating the liquid from the solid adsorbent.

Adsorbents

In the invention adsorbents are used that are capable of physically adsorbing ammonia. This is important, in the sense that one of the desires addressed by the invention, is avoiding the formation of further by-products, and thus the formation of products of a chemical reaction of ammonia are avoided.

Adsorbents capable of physically adsorbing ammonia are known in the art, and are well available to the skilled person. Suitable adsorbents include, but are not limited to, zeolites, alumina, silica gel, and activated carbon.

Adsorption of small molecules, like ammonia, is best achieved if the adsorbents pores are of the same size. In terms of pore size distribution, zeolites and activated carbon are preferred for the adsorption of ammonia.

In the process of the invention, the adsorbent is regenerated by dissolving ammonia adsorbed thereon in water. In the case of activated carbon, it is preferred with a view to this regeneration, to make use of un-impregnated carbon.

In zeolites the aperture size is between 3 and 8 Å depending on the amount of water and type of cations in the pores. The adsorption ability of zeolites can be modified by different processes of which ion exchange and dealumination are the most common. The pore size is preferably modified to fit the molecule diameter of the desired adsorbate, i.e. ammonia. This is best performed by ion exchange, where the cations captured in the structure are exchanged for ions of a different size. An example is the use of zeolite NaA (type A zeolite with sodium ions); herein the sodium ions are exchanged for calcium ions in order to increase the aperture size, or potassium ions in order to decrease the aperture size. The skilled person is well aware of these and other ways to tailor the pore size of a given zeolite to the desired adsorbate.

The regular and relatively small size of the apertures contributes to zeolites being well adjusted for ammonia adsorption. Also, high alumina zeolites of type A and X are suitable for ammonia removal due to their electrostatic interactions and the large dipole moment of ammonia. In view of the potential influence of water in the zeolites on the cation sites since, as it can block pores, the zeolites are preferably dehydrated prior to adsorption. Zeolites of type A and X are the most suited zeolites for ammonia adsorption at temperatures between 25 and 120° C. Ammonia adsorption can be increased by acid pre-treatment of the zeolite since the ammonia then can be protonated prior to the ammonium adsorption and the ammonia adsorption on to the surface then would increase.

As mentioned above, it is not excluded (nor undesirable), if an adsorbent, in addition to being capable of physically adsorbing ammonia, also binds ammonia through chemical adsorption. In the invention this does not lead to an unwanted by-product, as the adsorbent is regenerated through the removal of physically adsorbed ammonia, and is thus reused irrespective of whether any chemisorbed ammonia is still present.

This particularly holds for zeolites, which are capable of strongly binding ammonia, exhibiting stronger interaction between the surface and ammonia than in the case of activated carbon. Zeolites are therefore preferred according to the invention. More preferably, the zeolite is selected from the group consisting of 4A zeolite and 13X zeolite, with the latter being the most preferred.

The adsorbent preferably is introduced in the form of particles, particularly comminuted particles, which have the advantage of good free-flowing properties in the gas-stream. It will be understood by the person skilled in the art that suitable particle sizes will differ per plant equipment and process design. Preferred particle sizes range from 1 µm to 100 µm. This ranges serves to allow the formation of a homogeneous filter cake on the filter cloth in the baghouse and provide a good balance between small particles that are desired so as to ensure that the solids are free flowing/dispersed in the gas stream and large particles so as to enable the solids to be dewatered without passing through the dewatering unit and ending up in the liquid stream.

The Contacting Step

The method of the invention comprises contacting the above-identified off-gas with a solid adsorbent. This step can be carried out in various manners.

It is also possible, e.g., to use a conventional adsorption technique, such as leading the gas stream over a fixed or a fluidized bed of adsorbent. Preferably, the adsorbent is introduced into the gas stream in the form of particles.

The introduction of the adsorbent into the gas stream in the form of particles is an uncommon way of working which, however, presents a judicious choice in the specific case of the off-gas of a urea plant finishing section. Normally, one would not readily consider introducing loose particles into a gas-stream that is to be purified. In the case of urea, the present inventors considered that the gas stream contains solids anyway, viz. urea dust. Since this implies the need for a solid-gas separation step, the introduction of yet another solid does not adversely affect the overall process simplicity and economy.

Rather, an advantage is that the loose particles allow the usage of separation techniques that also serve to remove urea dust, such as baghouse filters or cyclones. Moreover, the introduction of the adsorbent in the form of particles, particularly in combination with a baghouse filter, yields a further advantage in that, based on similar adsorption capacity, bulky adsorbent beds can be avoided.

Thus, in the process of the invention, the preferred course of action comprises injecting a comminuted adsorbent into the airstream of a urea production plant finishing section, and adsorb the ammonia. This injection of adsorbent into the airstream can be conducted, e.g., using a bulk-storage silo followed by feeders which transport the adsorbent from the silo to the injection point.

Adsorption of ammonia on activated carbon is favored at low temperatures and hence, the airstream is preferably cooled to enhance the adsorption if activated carbon is used. This can be achieved by addition of water forcing the temperature to decrease. The cooling water is evaporated from the injected adsorbent.

In the case of using zeolites as adsorbent, no air cooling is required since the working capacity is constant over a larger temperature range.

The Solid-Gas Separation Step

The method of the invention comprises separating the solid adsorbent having ammonia adsorbed thereon from the gas in which the adsorbent was introduced.

Methods and equipment to separate solids from gas are known to the skilled person. Particularly suitable technologies for use in the invention include baghouse filters and cyclones.

In the specific process of removing ammonia from the off-gas of a finishing section of a urea production plant, which gas essentially comprises both ammonia and urea dust, the use of solid adsorbents and the subsequent solid-gas separation has the advantage that not only the adsorbent, but also the urea dust is removed. This makes the use of additional equipment for the removal of dust, such as wet scrubbers, redundant, which clearly presents an advantage from the viewpoint of simplicity of the process, and from a viewpoint of process economy and equipment investments.

Whilst the use of cyclones is a relatively cheap way of conducting the solid-gas separation, a preferred method in accordance with the invention involves the use of one or more baghouse filters. Such filters are known in the art, and are used to remove powder or dust particles from airstreams. They are readily available to the skilled person without further elucidation. In addition to advantages for removal and regeneration of adsorbent, when a baghouse filter is used the actual adsorption is believed to be perfected by a filter cake of adsorbents on the bag, thus combining the advantages of adsorbent particles in a gas stream, and the function of a fixed bed of adsorbent.

In general, in a baghouse filter an airstream comprising particles is blown through a filter, either during a preset time period or until a pressure drop, which will occur due to the thickening of the filter cake formed, has reached a certain level. The skilled person will be able to select the appropriate design parameters. E.g., whether to blow or suck the air through the filter. When it comes to designing the filter, it is important to have enough spacing between the bags so that they do not rub against each other causing damage. Another parameter is the ratio between the airstream size and the cloth area. A too large ratio leads to particles penetrating the cloth, which results in increasing pressure drops. These particles are also very hard or impossible to wash out. The filtration area is decided by the number of bags as well as the diameter and length of the bag. Here it is important to realize that with larger bag sizes, the cleaning becomes more difficult.

The choice of fabric in the bag is another parameter that the skilled person will be able to judiciously choose. It is preferred to use bags with the right permeability and thickness for the process. The bags can be made out of natural or synthetic materials, and can be improved by different surface treatments. A suitable material, particularly when aiming at a long service life of the bags, is Teflon (poly tetra fluoro ethylene).

A characteristic of a baghouse filter that comes with advantages in the present invention, is associated with the fact that the regeneration of the adsorbent is done by dissolving ammonia, particularly in water, which can be conducted in the form of a washing step of filter cakes removed from the bags. A baghouse filter generally has a plurality of sections, which allows stopping the filtration—and removing the filter cake—in one section at a time, thus ensuring that the filtration process as such is continuous.

The filter is cleaned after the above-mentioned period of blowing air through it, and removal of the filter cake, usually by blowing air in pulses, through the filter in reversed direction. It will be understood that, preferably, also the cleaning is conducted in one section at a time.

In a preferred embodiment, one does not remove the entire filter cake each time, but only enough to decrease the pressure drop and enable regeneration of the adsorbent from the removed part of the filter cake. This ensures that also in the beginning of each cleaning cycle, the filtration is more efficient than if the filter cake were not present.

The Regeneration Step

As mentioned above, the method of the invention preferably also comprises a step of regenerating the solid adsorbent by dissolving ammonia in an extraction liquid, and separating the liquid from the solid adsorbent.

Suitable extraction liquids are generally ionic liquids, salt solutions, aqueous salt solutions, acidic salt solutions, acidified water and water. Preferably the extraction is done by water. Thus, both ammonia and urea can be dissolved. Preferably, the ammonia and the urea are re-used as well, as a reactant respectively as a product. The necessary techniques are well-known to the skilled person, e.g. ammonia removal by steam stripping and urea removal by concentrating through multiple evaporation steps Also the water used for the extraction can (for a great part at least) be re-used after further concentration of the remaining ammonia/urea solution.

Desorption is preferably conducted by mixing the adsorbent with the solvent in a well mixed tank. The ammonia will then be released and mixed with the solvent. Depending on the strength of the bonding of the ammonia to the adsorbent, the desorption methods can differ depending on what adsorbent that is to be used. E.g., it may be preferably to add heat when to desorbing ammonia from zeolites, e.g. by using water in the form of steam, whereas activated carbon could be desorbed using cooler water.

When using water as the extraction liquid, the particulate urea removed from the airstream will also dissolve.

After desorption, the mixture will consist of a slurry of the adsorbent and the solvent with dissolved ammonia and urea.

In order to remove the adsorbent from the slurry, created in the mixing tank, a solid-liquid unit separation will be applied. Several methods, known to the skilled person, are available to extract solid particles from a liquid. Preferred methods according to the invention include using a continuous vacuum filter, centrifugal filtration and centrifugal sedimentation.

Preferred types of filters are drum filters and rotary disc filters, Centrifuges generally come in two types, which both are suitable for use in the invention, viz. those that use a filtration method and those that work on the basis of a sedimentation principle, such as a vertical or horizontal bowl centrifuges. The filters and centrifuges that can be used in the invention is equipment well-known to the skilled person.

Re-Use of the Adsorbent

Whilst the regeneration of adsorbent as such does not preclude the regenerated adsorbent from being removed for different use, it will be clear that it is preferred in the present invention to actually re-introduce the regenerated adsorbent into the process of the invention. To this end, the adsorbent from which ammonia and urea is removed, and which has been subjected to a solid-liquid separation step mentioned above, will be re-injected into the airstream, i.e. re-used in the step of contacting the off-gas with a solid adsorbent in a next process cycle.

Considering that, generally, the production of urea is a continuous process, and thus also the emission of gas from the finishing section is, it will be understood that the term "next" implies a later point in time than the initial introduction before re-generation, and that the term "process cycle" refers to the cycle of introduction of the adsorbent, the contacting step, the solid-gas separation step, and the regeneration step. This cycle can also be referred to as the adsorbent cycle.

After the solid-liquid separation, in the case of using water as the extraction liquid, it is well possible in the process of the invention that the regenerated adsorbent is re-introduced in a wet state, although it will generally be recommendable to at least partially remove water, e.g. by filtration. However, if the adsorbent still contains water, the process of the invention presents an advantage in that the adsorbent is re-introduced into a hot gas-stream, viz. the off-gas of a urea production plant finishing section. The heat of the gas stream, which is inherently available, will ensure further evaporation of the moisture from the adsorbent. As a result, the adsorbent arrives at the stage of solid-gas separation (i.e. preferably in a baghouse filter) in a dry state, fully available for renewed adsorption of ammonia.

It will be understood that the moisture content of the adsorbent when introduced into the hot gas stream should preferably not be as high as to result in the gas being saturated with water before substantially all of the water from the adsorbent is evaporated. The person skilled in the art will be able, depending on circumstances such as the type of adsorbent, the temperature of the gas-stream, and the original water-content of the gas-stream, to determine the optimal moisture content of the adsorbent before re-introducing it into the gas-stream, and thus the desired extent of drying. In general, the moisture content of the adsorbent when introduced into the gas-stream is below 50% by weight, preferably below 30% by weight.

In the case of using a type of adsorbents the action of which includes chemical adsorption of ammonia, it is technically possible to include one or more steps serving to remove also at least some of the chemically adsorbed ammonia before re-using the adsorbent. E.g. with zeolites, one could use additional steam. However, as mentioned above, it is preferred according to the invention to not actively seek the removal of chemically adsorbed ammonia. An advantage hereof is not only the simplicity of the process, by avoiding the additional steps involved, but one also avoids additional energy input, which makes the process economically better viable.

As a result, when using zeolites, the process of the invention on start-up will involve virgin zeolites as the adsorbent, but after recycling the adsorbent will in fact be zeolite comprising chemically adsorbed ammonia. Whilst the sites available for chemical adsorption are thus occupied by a chemical unharmful to the urea production process (viz. ammonia), and a sufficient capacity for physical adsorption remains, the chemisorbed ammonia-loaded zeolite thus used, is in fact a very efficient adsorbent to achieve physical adsorption and regeneration of adsorbent in a process for the removal of ammonia from a finishing section of a urea production plant.

Further Aspects of the Invention

The invention, in another aspect, provides the use of a solid adsorbent capable of physically adsorbing ammonia, for the removal of ammonia from the off-gas of a finishing section of a urea production plant. Whilst such adsorbents are known for ammonia, it has not been recognized in the art to use particular physical adsorption on solid adsorbents to solve the specific problem of removing ammonia from the off-gas of a finishing section of a urea production plant, in which off-gas a difficulty resides in the low concentration of ammonia present.

A preferred embodiment of the use according to the invention is the use of zeolites, more preferably zeolite 13X.

Particularly, the invention in one embodiment provides the use of solid adsorbents, capable of physically adsorbing ammonia, for the removal of ammonia from the off-gas of a finishing section of a urea production plant in a method in which the solid adsorbent is regenerated by removing ammonia physically adsorbed thereon through liquid extraction, preferably by dissolution in water. A preferred embodiment of the use of regenerated adsorbent is the used of zeolites, more preferably zeolite 13X, comprising chemically adsorbed ammonia.

It will be understood that the use of adsorbents according to the invention can generally be done through the process steps described hereinbefore.

With reference to the process description above, it will also be understood how, in another aspect, the invention is carried out as a method for the removal of both ammonia and urea dust from the off-gas of a finishing section of a urea production plant.

The invention also pertains to a process for the production of urea comprising reacting ammonia and carbon dioxide under conditions so as to form urea and water, and subjecting the urea to a melt finishing step so as to form particulate urea and off-gas, wherein ammonia, and preferably also urea dust, is removed from the off-gas by a method in accordance with one or more of the embodiments described hereinbefore. The step of producing the urea itself, and the melt-finishing (prilling, granulation, pelletizing) mentioned previously, is well-known to the skilled person, and does not require elucidation here. Reference is made e.g. to a process as s described in European Chemical News, Urea Supplement of Jan. 17, 1969, pages 17-20. The step of removing the ammonia, and preferably also the urea dust, has been substantially described above.

It is to be understood that the invention is not limited to the embodiments as described hereinbefore. It is also to be understood that in the claims the word "comprising" does not exclude other elements or steps. Where an indefinite or definite article is used when referring to a singular noun e.g. "a" or "an", "the", this includes a plural of that noun unless something else is specifically stated.

The invention will be illustrated with reference to the following, non-limiting Example and the accompanying non-limiting FIGURE.

DESCRIPTION OF THE DRAWING

FIG. 1 presents a flow sheet of the process exemplified below. In a gas stream (1), being the off-gas of a finishing section of a urea production plant; solid adsorbent is injected (10) from a bulk storage tank (A) so as to render a gas stream (2) comprising said off-gas and said solid adsorbent; the gas stream with the adsorbent (2) is introduced into a baghouse filter (B); From the baghouse filter a gas stream (3) is emitted, being gas (air) from which solid adsorbent and urea dust have been removed; from the baghouse filter the solids (adsorbent and urea dust) are removed (4) in the form of filter cakes and collected in a silo (C); solids are then fed (5) into a dissolution tank (D) into which fresh water (6) is introduced so as to dissolve adsorbed ammonia as well as collected urea dust; from the dissolution tank a resulting liquid stream (7) being a slurry of water, with ammonia and urea dissolved, and adsorbent is fed into a (drum/disc) filter (E); from said filter a liquid stream (8) is collected being a concentrated solution of ammonia and urea in water, and a stream (9) is collected being adsorbent with remaining water, which is fed into the above-mentioned bulk storage tank (A); Not shown is the option to dry the adsorbent before introduction into the gas stream (1).

The sequence of streams (10), (2), (4), (5), (7), (9), and again (10), as running via the devices (A)-(B)-(C)-(D)-(E) together forms an adsorbent cycle, representing the use and the regeneration of the adsorbent in accordance with the invention.

In the drawing an optional stream (11) is depicted. This represents a possibility to recycle part of the solution collected from filter (E) back to the dissolution tank (D).

EXAMPLE

With reference to the scheme given in FIG. 1, the exemplified process makes use of a baghouse filter with pneumatic dust transmitters, a dust bin with screw feeder, a mixing tank, a rotary vacuum-filter, and feeders with a bulk-storage tank.

The off-gas from the granulator of a urea production plant is mixed with an adsorbent containing water. In order to separate the adsorbent from the airstream a baghouse filter is used. Here, all the particulate urea is removed co-currently with most of the gaseous ammonia. The former is removed by filtration and the latter is adsorbed on the adsorbent.

Adsorption of ammonia is accomplished by a filter cake of the adsorbent on the bags. When the gas passes through the filter cake, ammonia adsorbs similar to a process using a fixed bed. Design targets are more than 90% removal of ammonia and greater than 99.95% of the particulate urea. Since the urea dust is removed in the baghouse filter, the presently used scrubbers can be removed.

When the filter cake builds up, the pressure drop increases. By a pressurized jet-pulse the filter cake is partly removed in cycles controlling the pressure drop at 3500-4000 Pa. The magnitudes of pulses are adjusted in such a way that only small areas of the bags are cleaned in each cycle. Short cycles are preferable because they deliver the solids at a more continuous rate and the variations in ammonia emissions are much smaller. It is also important to remember that to prevent the hydrolysis reaction of the urea, short retention times are required.

The removed solids drop down to conical hoppers at the bottom of the baghouse filter and fall by gravitational forces into pneumatic conveyors. The conveyors operate intermittently to transport the solids into a silo, used as a buffer for the solids. Appropriate amounts of solids are screw-fed into a mixing tank into which water is added in order to dissolve the urea and ammonia.

The slurry from the mixing tank is fed to a rotary vacuum-filter which removes a concentrated water solution of urea and ammonia. Two parallel vacuum-filters is suggested, each capable of handling 100% of the total flow, of which one is used at all time. This would make it possible to clean or repair one of the filters without stopping the process entirely. The recovered solution is recycled back to the urea plant. A possibility could also be to recycle part of the solution to the dissolution tank to lower the amount of fresh water needed. The injection of adsorbent into the airstream is be conducted by feeders which transport the adsorbent from the bulk-storage to the airstream.

All units with an exception of the disc/drum filter are constructed of carbon steel due to its low cost and reasonably high durability. The disc/drum filter is made of stainless steel.

The design parameters for the baghouse filter are presented in the table below:

TABLE

| Design Parameter | Activated Carbon | Zeolites |
| --- | --- | --- |
| Water content, $x_2$ (kg/kg dry air) | 0.036 | 0.023 |
| $T_2$ (° C.) | 60 | 89 |
| Injected adsorbent (tons/hr) | 159 | 24.4 |
| Adsorbent in BH (tons) | 73.8 | 91.1 |
| Baghouse filter area (m2) | 4370 | 4650 |
| Number of bags | 1620 | 1730 |

Calculations based on an initial velocity through the filter cake of 2 cm/s showed that the required area of the baghouse filter is 13400 m² in the activated carbon case, while the zeolites requires 14300 m². The baghouse filter has a polymer/paint liner and the bags are made of a polyamide. The materials chosen increase the life time of the unit.

The silo is designed to be able to handle all the adsorbent in the baghouse system at any given time. This leads to a total volume of 200 m³ for the activated carbon case, as 73.8 tons sits in the baghouse filter. The amount of zeolites in the baghouse system at all times is 91.1 tons. This leads to a silo of 230 m³.

The dissolution tank has to be able to hold equal amounts of water and adsorbent. Since the silo is designed to hold all the adsorbent in the baghouse filter, the dissolution tank does not need to hold as much. 10% of the circulated activated carbon is handled in the mixing tank, leading to an amount of 16 tons at all times, why the calculated volume should be around 60 m³. The space time in the mixing tank is therefore 6 minutes. Considering that ammonia is more difficult to desorb from the zeolites, the space time in the dissolution tank is set to 30 minutes. This results in a volume of around 30 m³. This tank needs an agitator to keep the slurry well mixed. The power requirement is chosen to be 10 kW. The disc filter has a surface area of 120 m². The drum filter needed in the zeolite case is 6.6 m².

The calculations for the injection unit are based on a system made up of a bin with a screw feeder. This bin is set to be able to hold the total amount of circulated adsorbent, which means 370 m³ in the activated carbon case and 60 m³ in the zeolite case.

The removal efficiency of ammonia is well above 90%, with almost 95% being removed when zeolites are used as adsorbent. In addition to this, at least 99% of the urea is removed in the baghouse filter and can be recycled to the urea plant, making the scrubbers used in existing plants redundant.

As the described technology only involves handling of water, urea and ammonia, no polluting stream is produced.

The invention claimed is:

1. A method for the removal of ammonia from the off-gas of a finishing section of a urea production plant, comprising
   (a) contacting the off-gas with a solid adsorbent capable of physically adsorbing ammonia;
   (b) adsorbing said ammonia from said off-gas onto said solid adsorbent;
   (c) separating the solid adsorbent having ammonia adsorbed thereon from the gas;
   wherein the adsorbent is injected into the off-gas in the form of particles and wherein either:
   said method further comprises regenerating the solid adsorbent by dissolving ammonia in an extraction liquid, and separating the liquid from the solid adsorbent; or
   wherein said solid adsorbent is also capable of physically adsorbing urea dust, and said method further comprises adsorbing said urea dust from said off-gas onto said solid adsorbent.

2. The method according to claim 1, wherein the adsorbent is selected from the group consisting of activated carbon and zeolites.

3. The method according to claim 2, wherein the zeolite is selected from the group consisting of natural and synthetic faujasites.

4. The method according to claim 3, wherein the zeolite is zeolite 13X.

5. The method according to claim 1, wherein the step of separating the solid adsorbent having ammonia adsorbed thereon from the gas is conducted by means of a baghouse filter.

6. A process for the production of urea comprising reacting ammonia and carbon dioxide under conditions so as to form urea, and subjecting the urea to a melt finishing step so as to form particulate urea and off-gas, wherein ammonia, is removed from the off-gas by a method in accordance with claim 1.

7. The method of claim 1, wherein said solid adsorbent is also capable of physically adsorbing urea dust, said method further comprising adsorbing said urea dust from said off-gas onto said solid adsorbent.

8. The method according to claim 1, wherein said extraction liquid is water.

9. The process according to claim 6 wherein urea dust is removed from the off-gas by a method in accordance with claim 7.

10. The method of claim 1, said method further comprising regenerating the solid adsorbent by dissolving ammonia in an extraction liquid, and separating the liquid from the solid adsorbent.

11. The method according to claim 10, wherein the regenerated solid adsorbent is re-used in the step of contacting the off-gas with a solid adsorbent in a next process cycle.

12. The method according to claim 11, wherein the regenerated solid adsorbent comprises chemically adsorbed ammonia.

13. The method according to claim 10, wherein the adsorbent is selected from the group consisting of activated carbon and zeolites.

14. The method according to claim 13, wherein the zeolite is selected from the group consisting of natural and synthetic faujasites.

15. The method according to claim 14, wherein the zeolite is zeolite 13X.

16. A process for the production of urea comprising reacting ammonia and carbon dioxide under conditions so as to form urea, and subjecting the urea to a melt finishing step so as to form particulate urea and off-gas, wherein ammonia, is removed from the off-gas by:
   (a) contacting the off-gas with a solid adsorbent capable of physically adsorbing ammonia;
   (b) adsorbing said ammonia from said off-gas onto said solid adsorbent;
   (c) separating the solid adsorbent having ammonia adsorbed thereon from the gas
   (d) regenerating the solid adsorbent by dissolving ammonia in an extraction liquid, and separating the liquid from the solid adsorbent.

17. A process for the production of urea comprising reacting ammonia and carbon dioxide under conditions so as to form urea, and subjecting the urea to a melt finishing step so as to form particulate urea and off-gas, wherein ammonia and urea dust are removed from the off-gas by:
   (a) contacting the off-gas with a solid adsorbent capable of physically adsorbing ammonia and urea dust;

(b) adsorbing said ammonia and said urea dust from said off-gas onto said solid adsorbent;
(c) separating the solid adsorbent having ammonia and urea dust adsorbed thereon from the gas
(d) regenerating the solid adsorbent by dissolving ammonia and urea dust in an extraction liquid, and separating the liquid from the solid adsorbent.

* * * * *